(12) United States Patent
Darby et al.

(10) Patent No.: US 12,230,376 B2
(45) Date of Patent: Feb. 18, 2025

(54) MEDICAL DATA MANAGEMENT SYSTEM

(71) Applicant: Fisher & Paykel Healthcare Limited, Auckland (NZ)

(72) Inventors: Adam John Darby, Auckland (NZ); Donald Roy Kuriger, Auckland (NZ); Bernhard Florian Lamprecht, Auckland (NZ); Mark Samuel Hamilton, Auckland (NZ); Alex Young, Auckland (NZ); Benjamin Wilson Casse, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/347,453

(22) Filed: Jul. 5, 2023

(65) Prior Publication Data

US 2024/0145047 A1 May 2, 2024

Related U.S. Application Data

(63) Continuation of application No. 17/888,278, filed on Aug. 15, 2022, now Pat. No. 11,735,298, which is a
(Continued)

(51) Int. Cl.
*G16H 10/60* (2018.01)
*A61B 5/00* (2006.01)
(Continued)

(52) U.S. Cl.
CPC ........... *G16H 10/60* (2018.01); *A61B 5/0015* (2013.01); *A61B 5/4818* (2013.01); *G16H 15/00* (2018.01);
(Continued)

(58) Field of Classification Search
CPC .... G16H 10/60; G16H 15/0015; G16H 15/00; G16H 20/00; G16H 80/00; G16H 40/67;
(Continued)

(56) References Cited

U.S. PATENT DOCUMENTS 5,722,999 A 3/1998 Snell
6,016,449 A 1/2000 Fischell
(Continued)

FOREIGN PATENT DOCUMENTS

WO WO 2000/072181 A2 11/2000
WO WO 2009/055635 A1 4/2009

OTHER PUBLICATIONS

Australian Examination Report issued in Application No. 2015232051 dated Jan. 24, 2019 in 4 pages.
(Continued)

*Primary Examiner* — Jeffery A Brier
(74) *Attorney, Agent, or Firm* — Knobbe Martens Olson & Bear LLP

(57) ABSTRACT

Data related to the adherence of a patient to a therapy regime can be collected from multiple medical devices, each of which may have an incomplete data set with data entries associated with times. Each incomplete data set represents a portion of a complete data set. The data sets can be integrated to create a complete data set with data entries from each incomplete data set being arranged in a temporal sequence with respect to one another. A report may be generated, the report having the data entries of the complete data set or a function of the data entries of the complete data set.

20 Claims, 11 Drawing Sheets

Related U.S. Application Data continuation of application No. 16/891,921, filed on Jun. 3, 2020, now Pat. No. 11,450,418, which is a continuation of application No. 15/126,971, filed as application No. PCT/NZ2015/050029 on Mar. 18, 2015, now Pat. No. 10,734,104.

(60) Provisional application No. 61/955,046, filed on Mar. 18, 2014.

(51) Int. Cl.
    *G16H 15/00* (2018.01)
    *G16H 20/00* (2018.01)
    *G16H 40/67* (2018.01)
    *G16H 70/00* (2018.01)
    *G16H 80/00* (2018.01)

(52) U.S. Cl.
    CPC ............. *G16H 20/00* (2018.01); *G16H 40/67* (2018.01); *G16H 70/00* (2018.01); *G16H 80/00* (2018.01)

(58) Field of Classification Search
    CPC ...... G16H 70/00; G16H 20/40; A61B 5/0015; A61B 5/4818; A61B 5/4833
    See application file for complete search history.

(56) References Cited

U.S. PATENT DOCUMENTS

| | | |
|---|---|---|
| 7,044,129 B1 | 5/2006 | Truschel et al. |
| 7,149,773 B2 | 12/2006 | Haller |
| 7,647,237 B2 | 1/2010 | Malave et al. |
| 8,015,972 B2 | 9/2011 | Pirzada |
| 8,821,433 B2 | 9/2014 | Bloomquist |
| 9,550,031 B2 | 1/2017 | Van Sickle et al. |
| 9,610,417 B2 | 4/2017 | Kassatly et al. |
| 9,730,632 B1 | 8/2017 | Kayyali et al. |
| 10,734,104 B2 | 8/2020 | Darby et al. |
| 11,450,418 B2 | 9/2022 | Darby et al. |
| 11,735,298 B2 * | 8/2023 | Darby .................... G16H 10/60 705/2 |
| 2002/0193679 A1 | 12/2002 | Malave et al. |
| 2003/0236450 A1 | 12/2003 | Kocinski |
| 2005/0061319 A1 | 3/2005 | Hartley et al. |
| 2005/0188083 A1 | 8/2005 | Biondi et al. |
| 2007/0055324 A1 | 3/2007 | Thompson et al. |
| 2007/0299358 A1 | 12/2007 | Bertinetti et al. |
| 2008/0033751 A1 | 2/2008 | Greene et al. |
| 2008/0058661 A1 | 3/2008 | Bardy |
| 2008/0097550 A1 | 4/2008 | Dicks et al. |
| 2008/0114689 A1 | 5/2008 | Psynik |
| 2008/0269841 A1 | 10/2008 | Grevious et al. |
| 2011/0087756 A1 | 4/2011 | Biondi et al. |
| 2012/0310674 A1 | 12/2012 | Faulkner et al. |
| 2013/0110924 A1 | 5/2013 | Steinhauer et al. |
| 2013/0267792 A1 | 10/2013 | Petersen et al. |
| 2014/0000609 A1 | 1/2014 | Steinhauer et al. |
| 2014/0156228 A1 | 6/2014 | Molettiere et al. |
| 2016/0285985 A1 | 9/2016 | Molettiere et al. |
| 2020/0294641 A1 | 9/2020 | Darby et al. |
| 2022/0392592 A1 | 12/2022 | Darby et al. |

OTHER PUBLICATIONS

International Search Report; PCT/NZ2015/050029; dated May 25, 2015; 4 pages.

Ieee, https://ieeexplore.ieee.org/document/7867920, IEEE Standard for Health Informatics-Point-of-care medical device communication-Part 10101, pp. 1-2. Jan. 15, 2005 (Year: 2005).

Engleman HM, Martin SE, and Douglas NJ. Compliance with CPAP therapy in patients with the sleep apnoea/hypopnoea syndrome. https://www.ncbti.nlm.nih.gov/pubmed/8202884. p. 1, Mar. 1994 (Year: 1994).

UK Examination Report for Application No. GB 1617553.1 dated Nov. 11, 2020, 2 pages.

* cited by examiner

MEDICAL DATA MANAGEMENT SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field of the Invention

The present invention generally relates to medical devices. More particularly, the present invention relates to systems for the management of medical device data.

Description of the Related Art

In the long term treatment or monitoring of medical conditions, it is common for healthcare systems to handle such conditions on an outpatient basis, e.g. at a residence of a patient rather than at a healthcare facility. To treat or monitor the patient on an outpatient basis, the patient may be prescribed a medical device that she may order from a medical device distributor or manufacturer and use at her place of residence. In many cases, if the patient is covered under a health insurance policy, the cost of the medical device may at least in part be paid or reimbursed by an insurer. In some cases, the cost of the medical device may at least in part be paid or reimbursed by a public healthcare system. The medical device may help the patient manage her medical condition by providing therapy or by obtaining and providing diagnostic data to a physician or healthcare provider. In some cases, the medical device may be given to the patient by a medical device distributor, who may offer the patient the device without immediate compensation, but who may be paid later by the insurer and/or healthcare provider. However, if the patient does not use the medical device on a regular basis to aid in the management of her medical condition, the management of the medical condition may be less effective. To help to ensure that the funds allocated by the insurer and/or healthcare system to at least in part purchase the medical device are well spent, the insurer and/or healthcare system may require the patient to provide evidence of regular use of the medical device. If the patient cannot provide proper evidence of regular use of the medical device, the insurer and/or healthcare system may opt to not subsidize the medical device purchase. The medical device distributor may not be paid and may be forced to repossess the medical device. Additionally, in some cases, if the patient engages in hazardous work or work requiring careful attention to detail, the patient's employer may require evidence of regular use of the medical device. If the patient cannot provide proper evidence of regular use of the medical device, to reduce the employer's liability, the employer may be forced to terminate the patient's employment. Furthermore, if the patient requires a license to engage in the work, the patient's license to handle the particular line of work (normally issued by a local or state government body) may be rescinded.

As such, it is important to be able to provide evidence of use of a medical device. This evidence may come in the form of a set of data indicating when and/or how the medical device was used over a period of time. This evidence may be referred to as the evidence of compliance or adherence, and the set of data may be referred to as compliance or adherence data (hereinafter, in this section referred to as evidence of compliance and compliance data, respectively). To both aid the patient in collecting and managing compliance data and reassure the medical device distributor that servicing the patient will result in reimbursement, many medical devices offer compliance data management solutions. In some cases, the medical device may automatically record the compliance data over the time period over which the patient uses the device and upload the data to a removable storage medium. The removable storage medium may be given to a physician, insurer, and/or medical device distributor. In some cases, the medical device may output encoded messages that the patient may manually input into compliance monitoring database, which may be on the internet, on a handheld monitoring device, or elsewhere. In some cases, the medical device may automatically wirelessly transmit compliance data to a compliance monitoring database through the use of wireless data communications technologies.

SUMMARY OF THE INVENTION

Some patients may wish to carry multiple medical devices that may be used interchangeably to treat and/or monitor their medical condition. In some cases, the patient may want a first high-end medical device to treat her condition at home and a second smaller or 'more travel-friendly' device to use when away from home for an extended period of time. For example, when considering obstructive sleep apnea (OSA), a patient who is a truck driver may wish to use a high-end positive airway pressure (PAP) device to treat her OSA at home and wish to use a lightweight travel-friendly PAP device to treat her OSA when working or otherwise away from home. However, compliance data management may become more difficult when two or more medical devices are used. In some cases, if the patient uses multiple devices over a given time period, the patient may forget to send compliance data for one or more of the devices and, in such cases, there may be gaps in the compliance data reported to a recipient (e.g., an insurer, a medical device distributor, etc.). In some such cases the patient may have more difficulty providing proper evidence of compliance to the recipient. In some cases, the patient may be forced to send two separate sets of compliance data and the recipient may have the added challenge of manually integrating the two sets of data to compile a single set of accurate compliance data. In either case, the tasks related to compliance data management may become more inconvenient for the patient and/or for the recipient. Accordingly, it is an object of the disclosure to provide improved data management solutions that may solve one or more of the above problems, or at least provide the public with a useful choice.

In accordance with at least one of the embodiments disclosed herein is a method of integrating data from two or more medical devices comprising: receiving a first data set comprising one or more data entries related to the use of a first medical device, related to the therapy of a patient using the first medical device, and/or related to a patient using the first medical device, each of the one or more data entries being associated with a time and/or a position in a sequence of entries, receiving a second data set comprising one or more data entries related to the use of a second medical device, related to the therapy of a patient using the second medical device, and/or related to a patient using the second medical device, each of the one or more data entries being associated with a time and/or a position in a sequence of entries, and integrating the first data set with the second data set to create a third data set, the integration being such that the third data set comprises the data entries of the first and second data sets.

In some configurations a report is generated comprising the third data set and/or a function of the data entries of the third data set.

In some configurations the integration is such that the third data set comprises the data entries of the first and second data sets arranged in a temporal sequence with respect to one another.

In some configurations the first and second medical devices are PAP devices.

In some configurations the first data is received from a first device.

Optionally the first data is received from the first device via an internal and/or peripheral data communications module of the first and/or a second device.

In some configurations the first data is received from the first device via an intermediary device.

In some configurations the first device is one of:
the first medical device, or
a proxy device.

In some configurations the second data is received from a second device. Optionally the second data is received from the first device via an internal and/or peripheral data communications module of the second and/or first devices.

In some configurations the second data is received from the second device via an intermediary device.

In some configurations the second device is one of:
the second medical device, or
a proxy device.

In some configurations the first data set is received at the second device.

In some configurations the second data set is received at the first device.

In some configurations the first and/or second data sets are received at a third device, such as a server.

In some configurations the report comprises information related to the adherence of a patient to a therapy regime.

In some configurations if the third data set comprises more than one data entry associated with the same time, a fault signal is generated.

In some configurations all of the data entries of the first set and all of the data entries of the second set are related to the same patient.

In some configurations the third data set is sent to both the first device and the second device.

In some configurations the first and second data sets are overwritten by the third data set.

In some configurations the function of the data entries of the third data set comprises an indicator related to the adherence of a patient to a therapy regime.

In some configurations the indicator comprises a binary indicator indicating the adherence of a patient to a therapy regime relative to a threshold level of adherence.

In some configurations the indicator comprises a qualitative indicator related to the degree of adherence of a patient to a therapy regime.

In some configurations the method of data integration is performed by the first device and/or by the second device.

In some configurations the method of data integration is performed by a third device remote from the first device and/or the second device, the third device optionally being the intermediary device.

In some configurations the method or system further comprises identifying data entries of the first data set that are coincident with data entries of the second data set based on a time stamp recorded for each data entry using clocks in the first and second devices.

In some configurations the method or system further comprises synchronizing a clock in the first device with a clock in the second device. Optionally, the clocks are synchronized by coupling the first and second devices. Optionally the clocks are synchronized using external time signals, such as GPS timing signals.

In some configurations, a time stamp window is used to identify coincident data entries that have time stamps with time stamp windows that overlap.

In some configurations, the plausibility of data entries from the first and second devices is determined based on the time difference between the respective data entry time stamps, and the respective geographical locations of the first and second devices. In some configurations, an anomaly is determined if the data entries from the first and second devices are within a time window (time range) that is commensurate with the geographical separation of the devices. In some configurations, the window is set manually or automatically based on the geographical separation. In some configurations, the time window is set using a look up table correlating time ranges for geographical separations. The geographical separations could be determined using GPS location technology on each device.

In accordance with at least one of the embodiments disclosed herein is a data management system comprising a controller configured to: receive a first data set comprising one or more data entries related to the use of a first medical device, related to the therapy of a patient using the first medical device, and/or related to a patient using the first medical device, each of the one or more data entries being associated with a time and/or a position in a sequence of entries, receive a second data set comprising one or more data entries related to the use of a second medical device, related to the therapy of a patient using the second medical device, and/or related to a patient using the second medical device, each of the one or more data entries being associated with a time and/or a position in a sequence of entries, and integrate the first data set with the second data set to create a third data set, the integration being such that the third data set comprises the data entries of the first and second data sets.

In some configurations the controller is configured to generate a report comprising the third data set and/or a function of the data entries of the third data set.

In some configurations the controller is configured to integrate the first data set with the second data set such that the third data set comprises the data entries of the first and second data sets arranged in a temporal sequence with respect to one another.

In some configurations the first and second devices are PAP devices.

In some configurations the first data is received from a first device. Optionally the first data is received from the first device via an internal and/or peripheral data communications module of the first and/or a second device.

In some configurations the first data is received from the first device via an intermediary device.

In some configurations the first device is one of:
the first medical device, or
a proxy device.

In some configurations the second data is received from a second device. Optionally the second data is received from the first device via an internal and/or peripheral data communications module of the second and/or first devices.

In some configurations the second data is received from the second device via an intermediary device.

In some configurations the second device is one of:
the second medical device, or
a proxy device.

In some configurations the first data set is received at the second device.

In some configurations the second data set is received at the first device.

In some configurations the first and/or second data sets are received at a third device, such as a server.

In some configurations the report comprises information related to the adherence of a patient to a therapy regime.

In some configurations if the third data set comprises more than one data entry associated with the same time, a fault signal is generated.

In some configurations all of the data entries of the first set and all of the data entries of the second set are related to the same patient.

In some configurations the third data set is sent to both the first device and the second device.

In some configurations the first and second data sets are overwritten by the third data set.

In some configurations the function of the data entries of the third data set comprises an indicator related to the adherence of a patient to a therapy regime.

In some configurations the indicator comprises a binary indicator indicating the adherence of a patient to a therapy regime relative to a threshold level of adherence.

In some configurations the indicator comprises a qualitative indicator related to the degree of adherence of a patient to a therapy regime.

In some configurations the first and second data sets are each associated with a patient.

In some configurations the first and second data sets are associated with the same patient.

In some configurations if the first and second data sets are not associated with the same patient, a fault signal is generated.

In some configurations if the first and second data sets are not associated with the same patient, the report comprises an error message.

In some configurations the first device is the first medical device and the second device is the second medical device.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

Certain features, aspects and advantages of at least one of the configurations disclosed herein include the realization that partial sets of compliance data can be taken from multiple separate medical devices and integrated such that a single complete set of compliance data can be obtained. The single complete set can be transferred to one or more of the medical devices, to a physician, to an insurer, or to another person, apparatus, or system. In some cases, a report disclosing the adherence of a patient to a therapy regime may be generated. The report may be sent to one or more of the medical devices, to a physician, to an insurer, or to another person, apparatus, or system.

Figure 13:
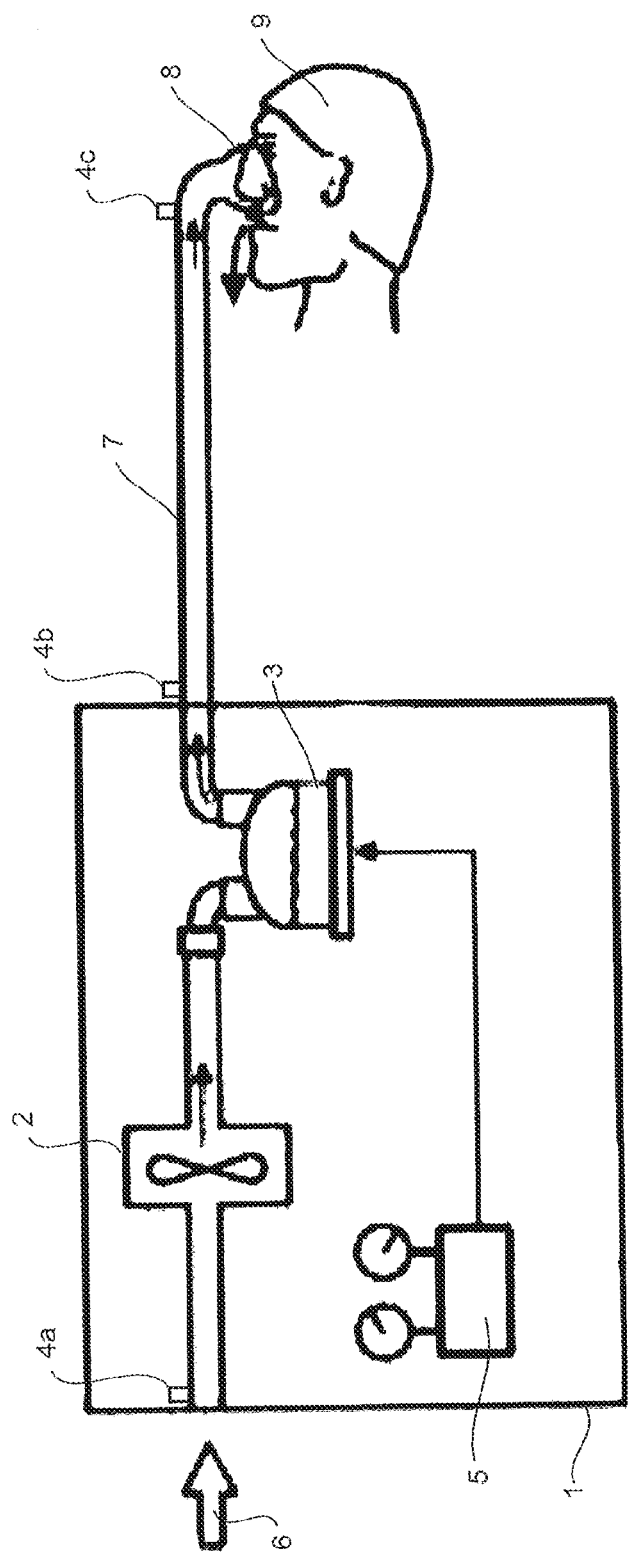
FIG. 13 is an illustration of a medical device (e.g. a breathing assistance apparatus).

Embodiments described herein relate to merging data from two or more medical devices, such as (but not limited to) a breathing assistance apparatus 102/108 shown schematically in FIG. 13. The breathing assistance apparatus 102/108 shown in FIG. 13 could be a pressure therapy apparatus (such as a CPAP apparatus or similar) or it could be a flow therapy apparatus. Either way, the apparatus comprises a housing 1 with a flow generator 2 (blower), humidifier 3, sensors (in suitable locations such as 4a, 4b, 4c) and a controller 5 for controlling the flow generator 2 and humidifier 3. The controller 5 operates the flow generator 2 to draw in ambient gas 6 (e.g. air) and pass a flow of gases through the humidifier 3 which is operated to humidify the gases. The gases are delivered to a patient 9 via a delivery conduit 7 and patient interface 8. Various flow, humidity, temperature, pressure and other sensors 4a-4c can be arranged throughout the system to provide feedback to the controller 5 for control of the flow generator 2 and/or humidifier 3. In a pressure therapy apparatus, the patient interface 8 forms a seal around the mouth and/or nose of the patient 9 and the controller 5 controls the flow generator 2 to create a controlled pressure for delivery to the patient interface 8 and ultimately the patient 9. In a flow therapy apparatus, the controller 5 operates the flow generator 2 to create a controlled flow for delivery to the patient interface 8 and ultimately the patient 9.

Figure 1:
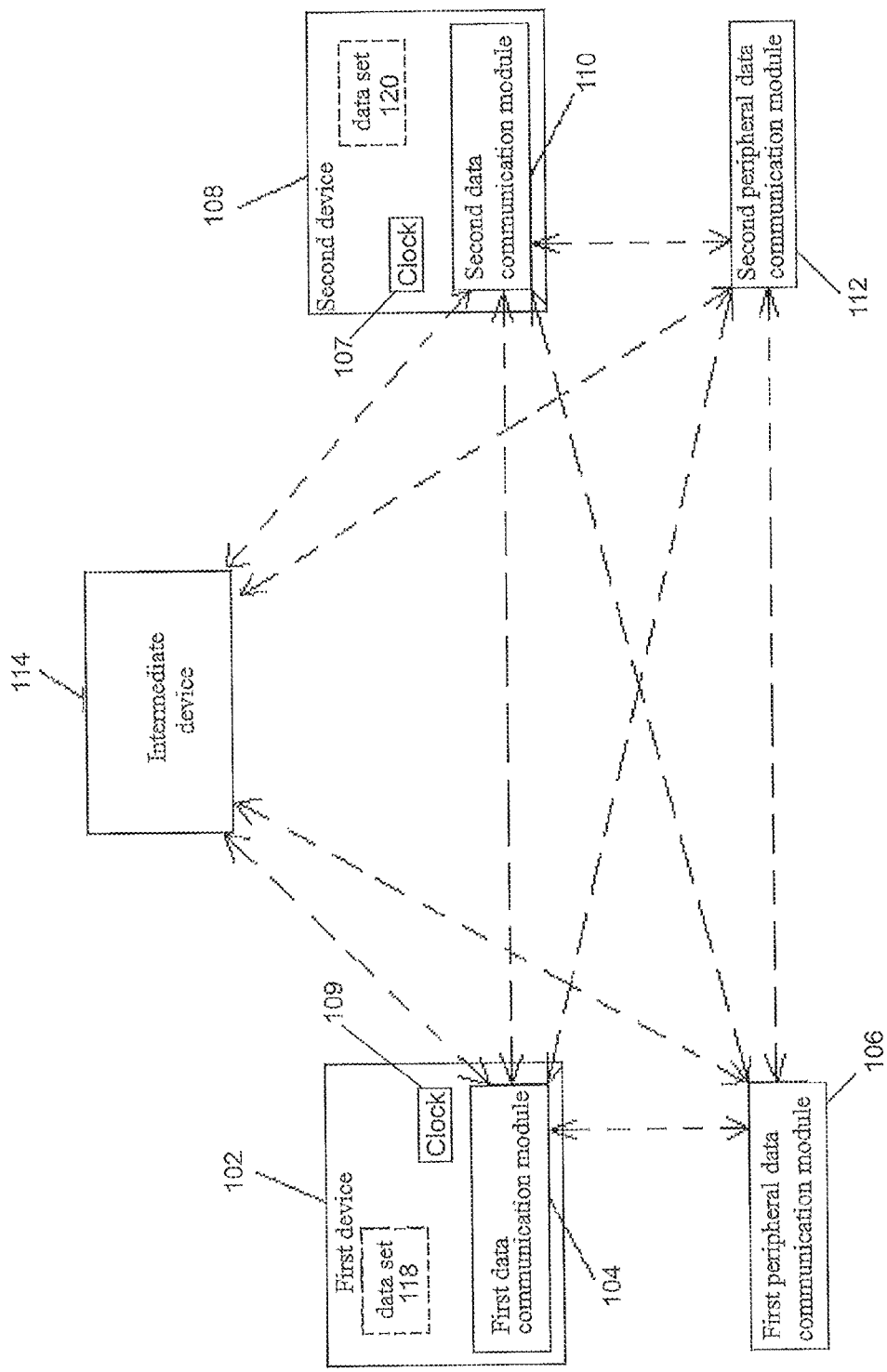
FIG. 1 is schematic diagram of a data communication system.

With reference to FIG. 1, a schematic diagram of a data communication system involving a plurality of devices (such as shown in FIG. 13) is shown. A first device 102 is illustrated. The first device 102 may be a medical device, e.g., a positive airway pressure (PAP) therapy device. The first device 102 may comprise a first data communication module 104. The first data communication module 104 may directly and/or indirectly send and/or receive data to and/or from other devices. In some configurations, the first data communication module 104 may be a part of or integrated with the first device 102. In some configurations, a first peripheral data communications module 106 may be physically connected (e.g. through wired communication technologies such as USB, RS232, Ethernet, I2C, and/or other technologies) and/or wirelessly connected (e.g. through wireless communication technologies such as Bluetooth, WiFi, near field communications (NFC), and/or other technologies) to the first device 102. The first peripheral data communications module 106 may directly and/or indirectly send and/or receive data to and/or from other devices. A second device 108 is illustrated. The second device 108 may be a medical device, e.g. a positive airway pressure (PAP) therapy device. Similarly, the second device 108 may comprise a second data communication module 110. The second data communication module 110 may directly and/or indirectly send and/or receive data to and/or from other devices. In some configurations, the second data communication module 110 may be a part of or integrated with the second device 108. In some configurations, a second peripheral data communications module 112 may be physically connected (e.g. through wired communication technologies such as USB, RS232, Ethernet, I2C, and/or other technologies) and/or wirelessly connected (e.g. through wireless communication technologies such as Bluetooth, WiFi, near field communications (NFC) and/or other technologies) to the second device 108. The second peripheral data communications module 112 may directly and/or indirectly send and/or receive data to and/or from other devices. The first and second devices 102, 108 may communicate with each other. In some configurations, the first and second devices 102, 108 may communicate with each other through the first and second data communication modules 104, 110. The communication may be through the use of wired or wireless communications standards or technologies similar to those described above. In some configurations, the first device 102 may communicate with the second peripheral data communications module 112 through the first data communications module 104. In some configurations, the second device 108 may communicate with the first peripheral data communications module 106 through the second data communication module 110. In some configurations, the first 102 and second 108 devices might communicate with each other through the first 106 and second 112 peripheral data communications modules. Any of these communications may proceed via or through an intermediary device 114. The intermediary device 114 may be a medical device (e.g. a PAP device), a remote computing system (such as a desktop computer, a laptop computer, a tablet, a mobile phone, or a wearable computing system such as a 'smart watch'), a wide area network (WAN), such as the internet or a cloud computing network, or another intermediary device.

Data can be transferred as described above and/or shown in FIG. 1 for the purposes of merging data sets from two or more devices. Data merging can be done in the first device 102, the second device 108, the intermediary device 114, in one or more other devices, or in any combination of one or more of the aforementioned devices. It should be noted therefore that the intermediary device 114 may provide a communications conduit between the first 102 and second 108 devices, may conduct data merging, or both.

As shown in FIG. 1, a first data set 118 (which, for example, may be held in a memory media of the first device 102) may be transmitted from the first device 102 to the second device 108 using any of the communication channels described. For example, the first data set 118 could be transmitted directly between the first data communications module 104 and the second data communications module 110. Alternatively, in some configurations, the first data set 118 may be transmitted from the first device 102 through the first data communications module 104 to the first peripheral data communications module 106, and the first peripheral data communications module 106 may transmit the first data set 118 to the second device 108 through the second data communications module 110. In some configurations, the first data set 118 may be transmitted from the first device 102 through the first data communications module 104 to the first peripheral data communications module 106, then from the first peripheral data communications module 106 to the second peripheral data communications module 112, and then from the second peripheral data communications module 112 to the second device 108 through the second data communications module 110. In some configurations, data may be transmitted from the first device 102 through the first data communications module 104 to the second peripheral data communications module 112, and then to the second device 108 through the second data communications module 110. Other methods of transferring data can also be undertaken as previously described above and/or as shown in FIG. 1 or as previously described with reference to FIG. 1 for transferring the first data set 118. Equivalent methods to those described can also be used for transferring a second data set 120 (which may, for example, be held in a memory media of the second device 108) from the second device 108 to the first device 102. In some configurations, the first device 102 and the second device 108 may send the first data set 118 and the second data set 120 to the intermediary device 114 without communication between the first device 102 and the second device 108. The intermediary device 114 can act as a conduit to transfer data sets between the first and/or second devices 102, 108 and/or can process the data sets to merge it or facilitate the merging. Data merging could alternatively occur in the first and/or second devices 102, 108 and/or in another device.

The type or nature of the data (in the data sets) obtained, received, and/or transmitted by the first device 102 and/or the second device 108 is not limited. In some configurations, the data comprises data related to the adherence of a patient to a therapy regime. In some configurations, the first data may comprise data related to the use of the first device 102, data related to therapy of a patient using the first device 102, and/or data related to a patient using the first device 102. The second data may comprise data related to the use of the second device 108, data related to therapy of a patient using the second device 108, and/or data related to a patient using the second device 108. In some configurations, and as described with reference to FIG. 13, the medical devices may be PAP devices. The data may comprise, for example, compliance data, AHI (apnea-hypopnea index) data, sleep quality data, data related to the number of hours the medical devices were used, or other types of data.

Figure 2:
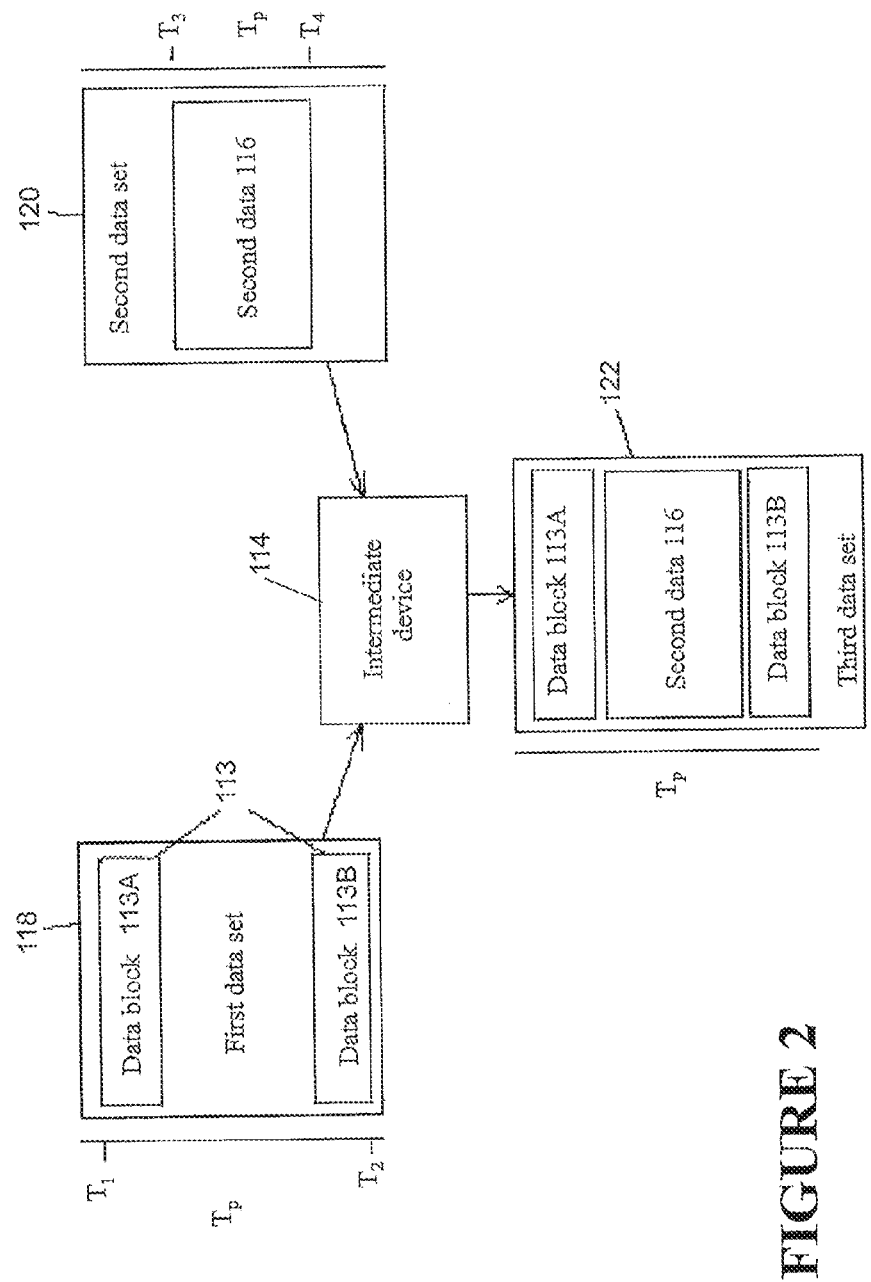
FIG. 2 is a schematic diagram illustrating a method of data synchronization.

The first and second data sets 118, 120 contain data in the form of one or more data entries, each optionally in one or more data blocks (see, e.g., FIG. 2). The data entries of the respective first and second data sets 118, 120 can be collected and/or recorded by the first and second devices 102, 108 or by other means. The first 102 and second 108 devices also each comprise a clock 109, 107. The clock can be anything that provides a timing reference/signal, and can be external or internal, and can be or comprise timing signals that originate from an external source (e.g GPS). Using the clock, each data entry receives a time stamp that associates the data entry with a time. Each data block, and data set can also receive a suitable time stamp. This provides a time and/or position of the each data entry, data block, and/or data set in a temporal sequence.

In alternative configurations, the first device 102 and/or second device 108 may not be medical devices. In some such configurations, the first and/or second devices 102, 108 may, for example, comprise proxy devices comprising data from medical devices (e.g. the medical devices described elsewhere in this disclosure with reference to FIG. 13). The proxy devices may receive data from the medical devices and integrate data received in a similar manner. Similar features, aspects and advantages of the systems, apparatus and methods of the present disclosure made with reference to the first and/or second devices 102, 108 being medical devices may be envisioned in some such cases where the first and/or second devices 102, 108 are not medical devices.

Figure 3:
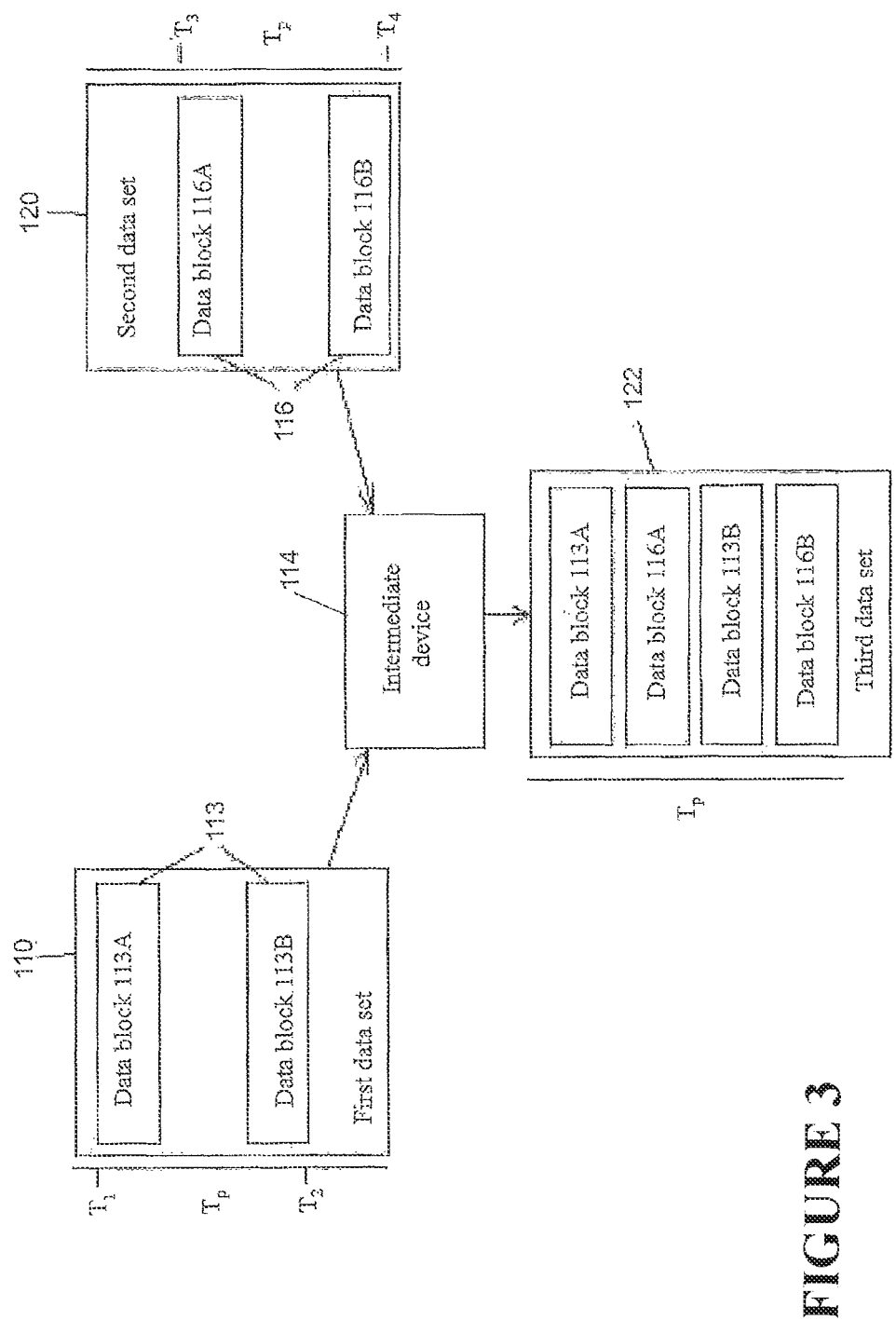
FIG. 3 is a schematic diagram illustrating a method of data synchronization.
Figure 4:
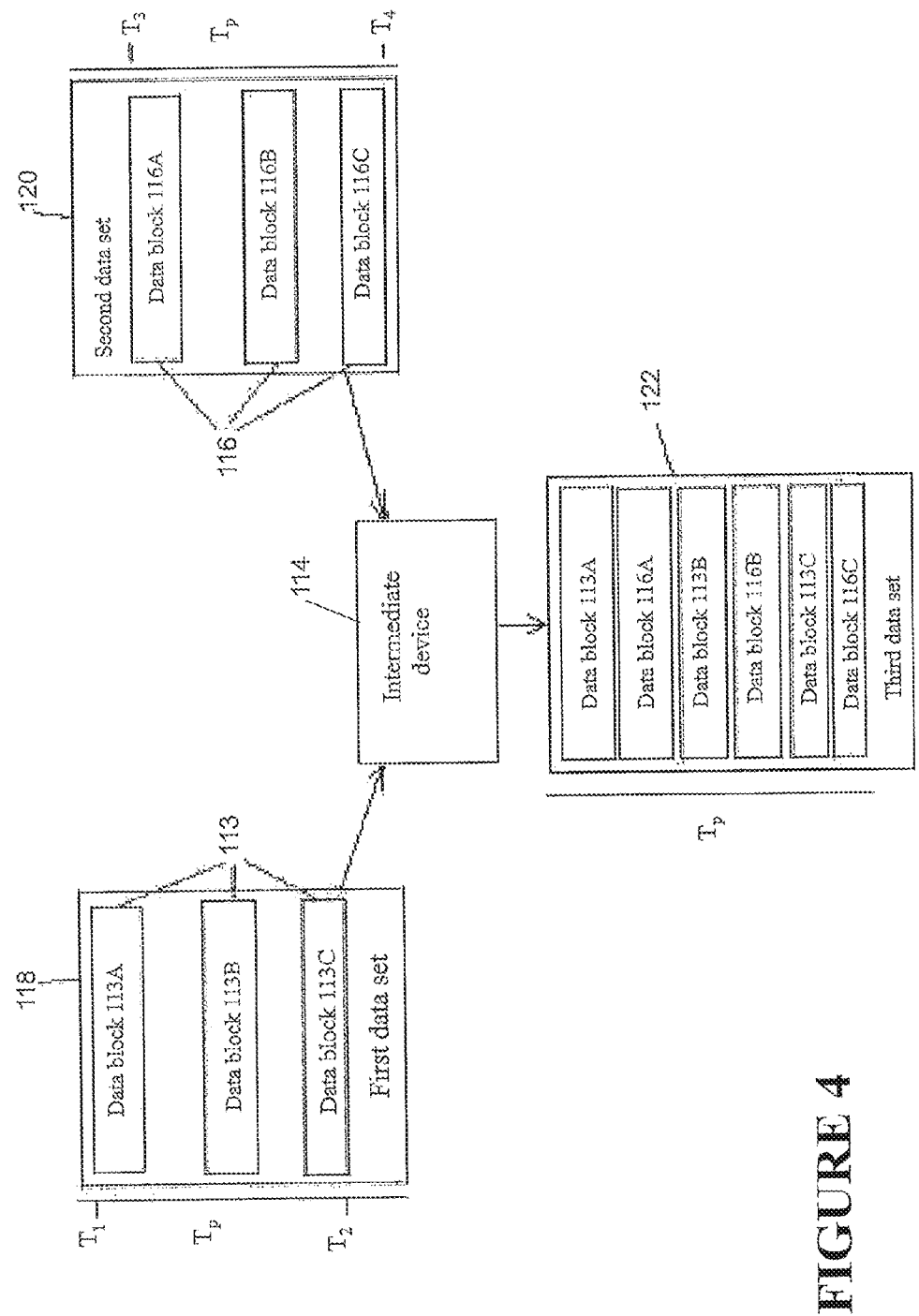
FIG. 4 is a schematic diagram illustrating a method of data synchronization.

FIG. 2 demonstrates a data integration method illustrating certain features, aspects and/or advantages of some configurations of the present disclosure. It should be understood that the word 'integration' or derivatives thereof may mean 'merging,' 'combining,' 'joining,' 'unifying,' 'compounding,' and/or 'amalgamating.' As described before, data can be transferred and/or merged by any of the devices of FIG. 1. As non-limiting example, a method of transferring data and merging it in the intermediary device 114 is shown in FIG. 2. A first-data set 118 is shown in FIG. 2. The first data set 118 may comprise a first data 113. The first data 113 may be obtained from the first device 102 over a period of time Tp. The first data 113 may comprise data blocks 113A, 113B, the data blocks 113A, 113B each comprising one or more time stamped data entries—that is, the data entries may each be associated with a time. The time may be when the particular data entry was created. A time can be associated with each data block and also the data set, either via time stamp or inferred from the data entry time stamps. In the illustrated configuration, the first data 113 may be noncontiguous between a first time T1 and a second time T2 over the period of time Tp, e.g., the first data 113 may comprise one or more gaps or missing entries in the first data 113 over the period of time Tp. The first data set 118 may be communicated by the first device 102 to the intermediary device 114. Similarly, a second data set 120 is shown. The second data set 120 may comprise a second data 116 obtained from the second device 108 over the period of time Tp. The second data 116 may be in the form of a block of data, the block of data comprising one or more data entries. The data entries may each be associated with a time. In the illustrated configuration, the second data set 120 may be contiguous between a third time T3 and a fourth time T4, but there may still be gaps or missing entries over the period of time Tp because the range of times bounded by the third time T3 and the fourth time T4 may be a subset of the period of time Tp. The second data set 120 may be communicated by the second device 108 to the intermediary device 114. The intermediary device 114 may compare the first data set 118 with the second data set 120. If the period of time Tp related to the first data set 118 is the same as the period of time Tp related to the second data set 120, and if the first and second data sets 118, 120 together do not comprise multiple data entries associated with the same time, then the intermediary device 114 may integrate the first and second data sets 118, 120 to create a third data set 122. The integration may be such that the data entries of the first data set 118 and the data entries of the second data set 120 are arranged in order such that the times associated with the data entries are set in a temporally sequential order with respect to one another. For example, in the illustrated configuration, the first and second data sets 118, 120 may be arranged such that the first data block 113A of the first data 113 comes first, the data block of the second data 116 comes second, and the second data block 113B of the first data 113 comes third, such that the third data set 122 comprises data entries of the first data 118 and the second data set 120 arranged in temporal succession and such that the third data set 122 represents a complete set of data spanning over the period of time Tp. As shown in FIG. 2, and the alternative examples of FIGS. 3 and 4, any number of data blocks or data entries of the first and second data sets 118, 120 may be integrated in a similar manner to create a third complete data set 122. In addition, it should be understood that the method of integration is not limited to two data sets, but any number of data sets from any number of devices may be integrated in similar manners to create a complete data set.

The third data set 122 may be used to generate a report comprising the entries of the third data set 122 and/or one or more functions of one or more entries of the third data set 122. For example, if the data of the first data set 118 and of the second data set 120 is related to the adherence of a patient to a therapy regime, the report may comprise information summarizing the patient's adherence to the therapy on a therapy session-by-therapy session basis, a night-by-night basis, or on some other basis. The report may comprise a binary indicator (e.g. 'yes,' 'no,' 'true,' 'false,' 'pass,' 'fail,' etc) derived from the data entries indicating whether the patient succeeded or did not succeed in achieving a level of adherence to a therapy regime relative to a threshold level of adherence. The report may comprise a qualitative indication (e.g. 'great,' 'good,' 'fair,' 'poor,' etc) derived from the data entries indicating the degree of adherence of a patient to a therapy regime. The degree of adherence may be compared to one or more threshold or baseline values to derive the qualitative indication.

Figure 6:
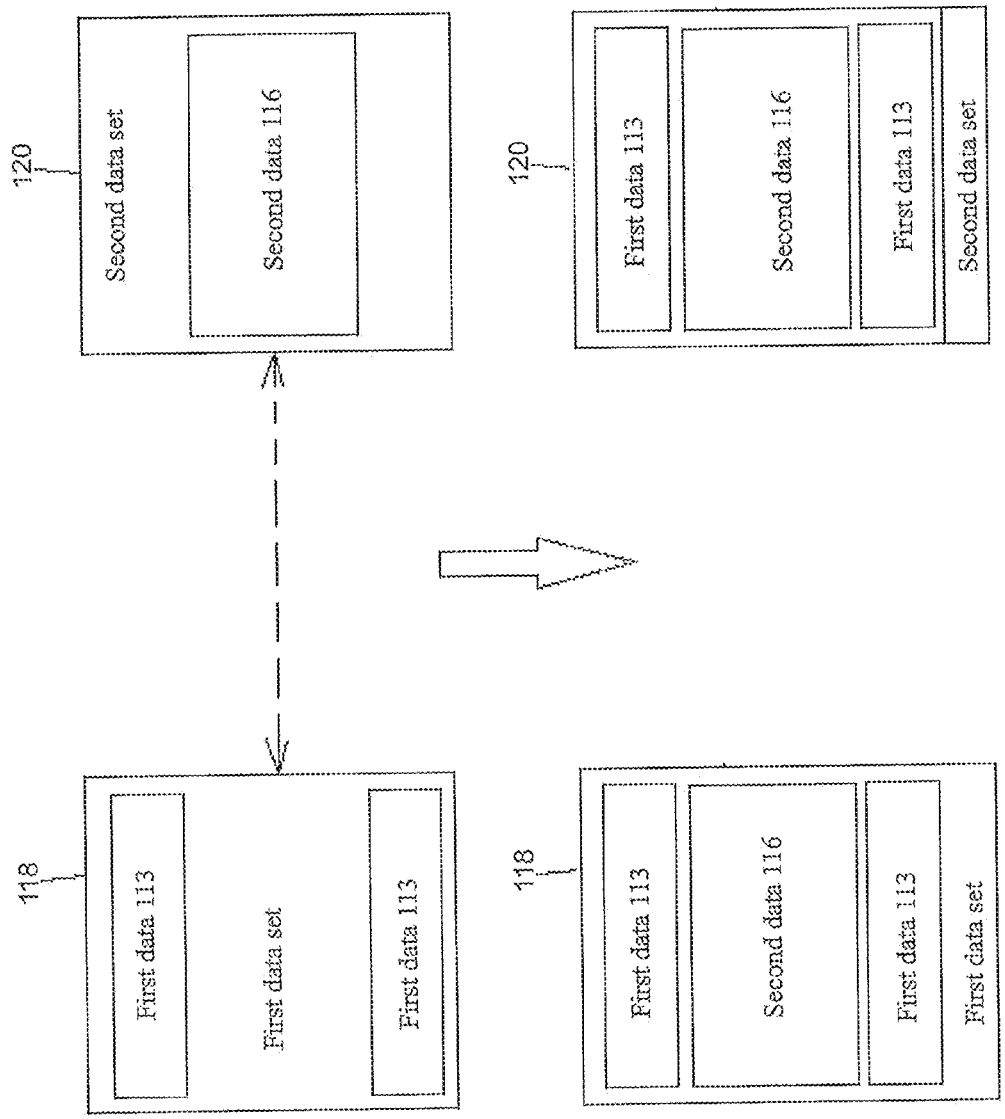
FIG. 6 is a schematic diagram illustrating a method of data synchronization.
Figure 9:
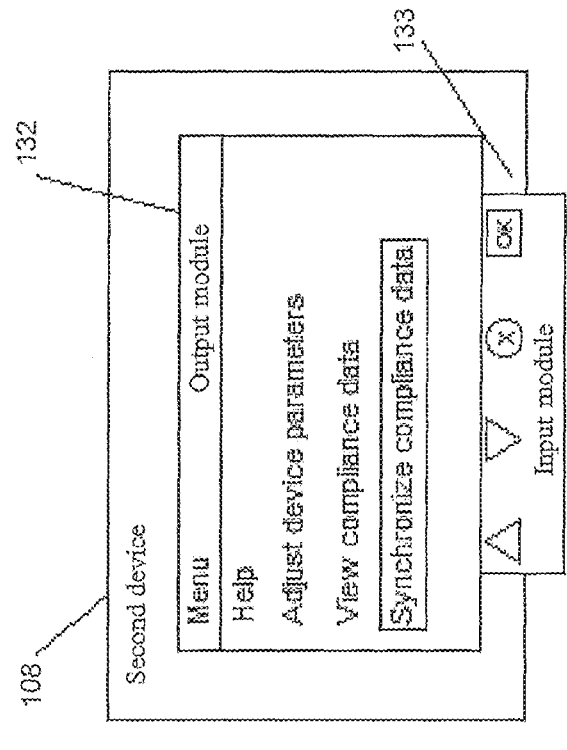
FIG. 9 is an illustration of an output module of a device.
Figure 12:
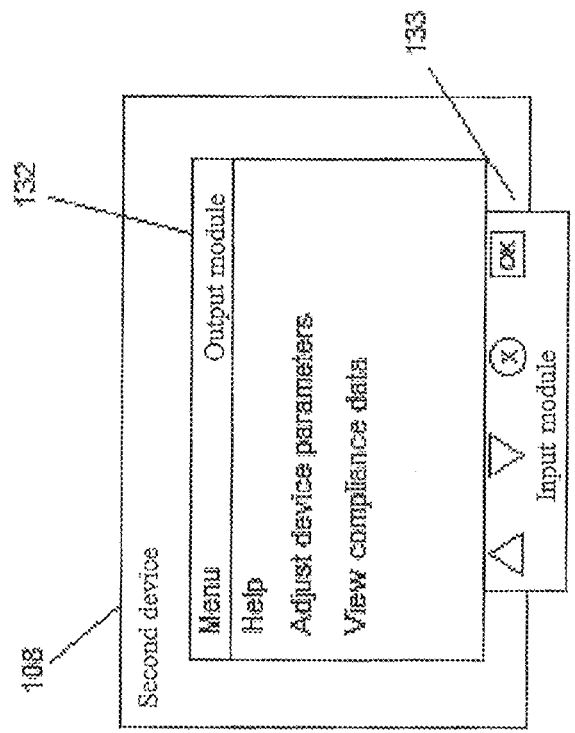
FIG. 12 is an illustration of an output module of a device.
Figure 11:
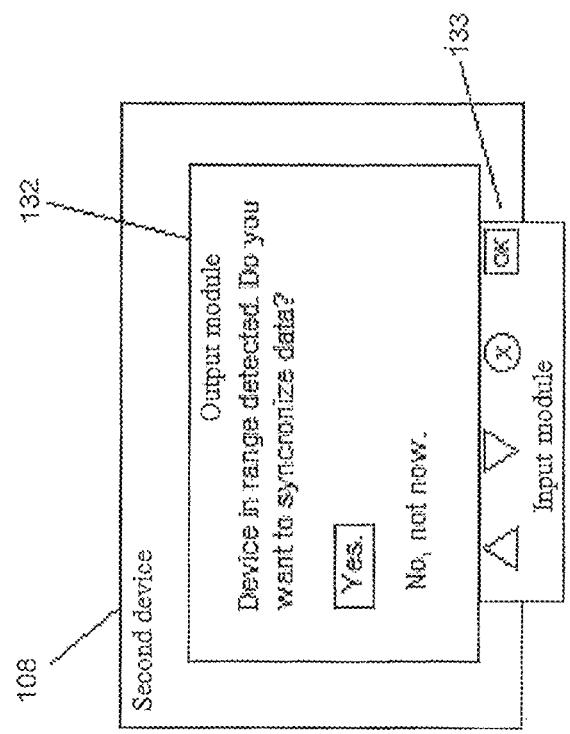
FIG. 11 is an illustration of an output module of a device.

It will be appreciated that using the intermediary device 114 and data transfer modes as described with respect to FIG. 2 is just one option. It will be appreciated other modes of transfer and merging data could be done alternatively. For example, in some configurations, and as illustrated in FIG. 6, a method of data integration similar to that illustrated in FIG. 2 and in the above passages may be used. However, instead of transferring data to an intermediary device 114 and formulating the third data set 122 at the intermediary device 114, in some configurations the first device 102 and the second device 108 may 'swap' data—in other words, the first device 102 may receive the second data set 120 from the second device 108 and the second device 108 may receive the first data set 118 from the first device 102. In some such configurations, data integration may occur at both the first device 102 and the second device 108 so that each of the first device 102 and the second device 108 comprises a copy of the third data set 122. The task of data management may then become easier for a user such as a patient because the user need only upload data from one of the devices rather than both of the devices—in addition, if the user misplaces one of the devices, a complete third data set 122 is still capable of being uploaded by the user using the other device. In some configurations, data may be transmitted in only one direction (e.g. transmission of the first data set 118 from the first device 102 to the second device 108 or transmission of the second data set 120 from the second device 108 to the first device 102). In some such configurations, the method of data integration may only take place at one of the devices. After data integration, the complete third data set 122 may be sent from one of the devices to the other device such that both devices have a copy of the third data set 122. In some configurations, the third data set 122 may overwrite the first data set 118 and/or the second data set 120 in the memory of the first device 102 and/or the memory of the second device 108. The first and second devices 102, 108 may communicate using many means, the means including wireless communication technologies such as Bluetooth, WiFi, near field communications (NFC) and/or other technologies. In some configurations, the method of data integration may proceed automatically. The first device 102 may automatically sense the presence of the second device 108, or likewise the second device 108 may sense the presence of the first device 102, and either device may automatically initiate the data integration method upon sensing the presence of the other device. In some configurations, if the presence of a device has been determined, one of the devices 102, 108 may prompt a user for input related to the data integration. For example, and as demonstrated in FIG. 11, the second device 108 may query the user for confirmation through an output module 132 of the second device 108, which may include one or more screens, microphones, and/or tactile indicators. A user, such as a patient, may use an input module 133 to respond positively or negatively to the query in order to authorize or decline the data integration (e.g., 'synchronization'). The input module 133 may comprise one or more buttons, knobs, dials, switches, levers, microphones, and/or touch screens allowing configuration of the second device 108. In some configurations, the user may manually request integration of the data sets. As demonstrated in FIG. 9, the request may proceed by using the input module 133 to navigate a menu of the output module 132 and/or select a data integration (e.g., 'synchronization') option. In some configurations, and as demonstrated in FIG. 12, if the presence of a compatible device is not determined, the option to integrate data may not be present, or may be obscured and/or not selectable by the user.

Figure 7:
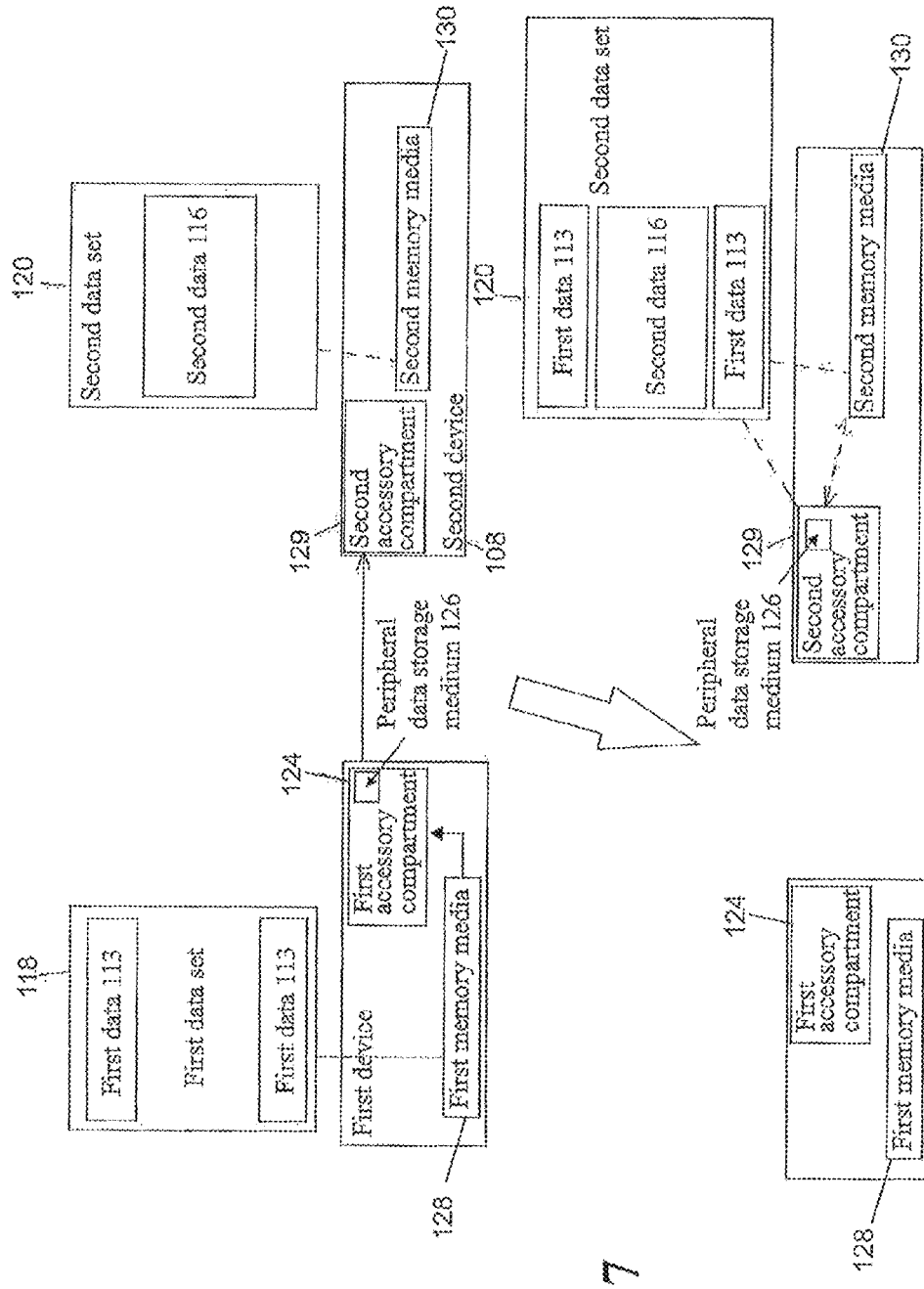
FIG. 7 is a schematic diagram illustrating a method of data synchronization.

In some configurations, and as illustrated in FIG. 7, a method of data integration similar to that illustrated in FIG. 2 and in the above passages may be used. However, instead of transferring data to an intermediary device 114 and formulating the third data set 122 at the intermediary device 114, in some configurations the first device 102 may copy the first data set 118 from a first memory media 128 of the first device 102 to a peripheral data storage medium 126. The peripheral data storage medium 126 may be inserted into a first accessory compartment 124 of the first device 102. The peripheral data storage medium 126 may be transferred from the first accessory compartment 124 of the first device 102 to a second accessory compartment 129 of the second device 108. The peripheral data storage medium 126 may communicate with a second memory media 130 of the second device 108 such that the second device 108 may perform the method of data integration using the first data set 118 stored on the peripheral data storage medium 126 and the second data set 120 stored on the second memory media 130. The complete third data set 122 obtained may be stored on the peripheral data storage medium 126. The peripheral data storage medium 126 may be removed from the second device 108 and may be physically given to a recipient (e.g. an insurer, a medical device distributor, a physician, or some other party) via mail, courier service, or via some other means. Again, it should be understood that this method of data integration is not necessarily limited to the use of only two devices. Data from any number of devices may be integrated.

Figure 8:
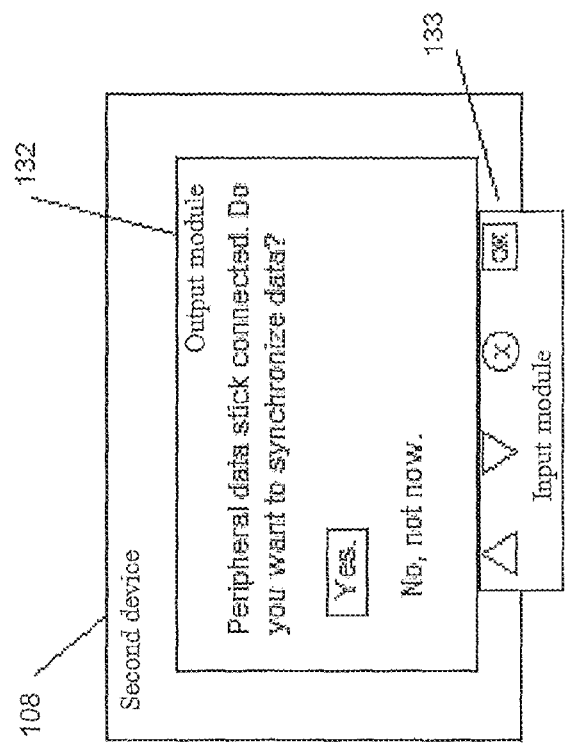
FIG. 8 is an illustration of an output module of a device.

Upon inserting the peripheral data storage medium 126 into the second accessory compartment 129 of the second device 108, the method of data integration of the first data set 118 and the second data set 120 may proceed automatically, e.g. without any involvement or input of/from the user. In alternative configurations, and as demonstrated in FIG. 8, the second device 108 may output a query to an output module 132 of the second device 108 which may include one or more screens, microphones, and/or tactile indicators. A user such as a patient may use an input module 133 to respond positively or negatively to the query in order to authorize or decline the data integration (e.g., 'synchronization'). The input module 133 may comprise one or more buttons, knobs, dials, switches, levers, microphones, and/or touch screens allowing configuration of the second device 108. In some configurations, and as demonstrated in FIG. 9, the user may manually request integration of the data sets. The request may proceed by using the input module 133 to navigate a menu of the output module 132 and/or select a data integration (e.g., 'synchronization') option. It should be understood that similar methods could be implemented using the first device 102 instead of the second device 108.

In the examples above, the data sets have data blocks with data entries that are not coincident in time. That is, the time stamps/time associated with each data entry is different from all the other entries. This is the normal situation—data entries should all have non-coincident times as two or more devices should not/cannot be used by the same person simultaneously. However, anomalous situations may arise where two or more data entries have coincident time stamps. Most likely, this means there is a problem. To improve data integrity, as described previously, during integration of the two or more datasets, data entries from different medical devices associated with the same time (coincident data entries) are identified for further action. It is useful to identify anomalous coincident data entries, as this indicates a possible error in the respective clocks, in data collection, in use of the devices or the like. It can indicate that the clocks are wrong, that different people are using the devices so the data entries do not relate to the same person and/or that data lacks integrity due to incorrect recordal, malfunction in either of the medical devices, and/or inadvertent or deliberate misuse of the medical devices. If two medical devices are geographically remote from each other, it is not possible for a patient to use both at once. Even if two devices are not remote, they cannot and should not be used simultaneously by the same person. Therefore, any data entries associated with the same time across two or more devices should be flagged as an error and/or follow up action taken. For example, a warning can be provided, coincident data deleted, or one coincident data entry can overwrite the other.

The integrity of this identification of coincident data entries relies on synchronization of the internal clocks of the medical devices from which each data set comes—otherwise, there can be no confidence that data entries with the same time stamp did in fact get recorded at the same time. In this case, there may not actually be a problem with coincident data entries, just a perceived problem which could lead to a false positive leading to unnecessary follow up action.

If the respective internal clocks of each medical device are not synchronized, this undermines the identification of coincident data entries. This can cause the following problems when merging data sets.

Coincident medical data entries that actually occur at the same time across different medical devices are not identified as such because the timestamps are not the same due to clock de-synchronization.

Non-coincident data entries that do not occur at the same time are incorrectly identified as being coincident as the unsynchronized clocks inadvertently record the same time for medical data entries that were in fact temporally separated.

The embodiments described herein can be adapted with one or a combination of the following to ameliorate the problems described above.

First, synchronization techniques can be used to synchronize the clocks of various medical devices. This could be achieved by physical, wireless or other communicative coupling between the medical devices continuously or periodically to synchronize the clocks. For example, the medical devices could communicate their clock signals via wireless technologies when in range of each other to effect synchronization. Alternatively, or additionally, GPS or other external timing signals could be used to create synchronized clock signals in the medical devices.

Second, when identifying coincidence of data entries from different medical devices, a time stamp window is optionally used to establish coincidence. This is useful for dealing with the problem of respective device clocks only being slightly de-synchronised. Rather than requiring an exact time match between the time stamps of two data entries to establish coincidence, a time window (tolerance or time range) is allowed around each time stamp. If the time window of each data entry being compared overlaps to at least some degree, then it is determined that the data entries are coincident in time. The time window could be any suitable window, such as the time stamp+/−1 second (or any other tolerance range between 0 and 1 second, or even a tolerance range above 1 second). The window should be specified to be large enough to compensate for a likely magnitude of de-synchronization, but not so large as to cause two non-coincident data entries to be falsely identified as coincident.

Other difficulties may arise when the first device 102 and the second device 108 are set to different times and/or are incapable of maintaining synchronicity with a reference time (e.g. a time found on an atomic clock, a time associated with a GPS signal, etc).

Figure 5:
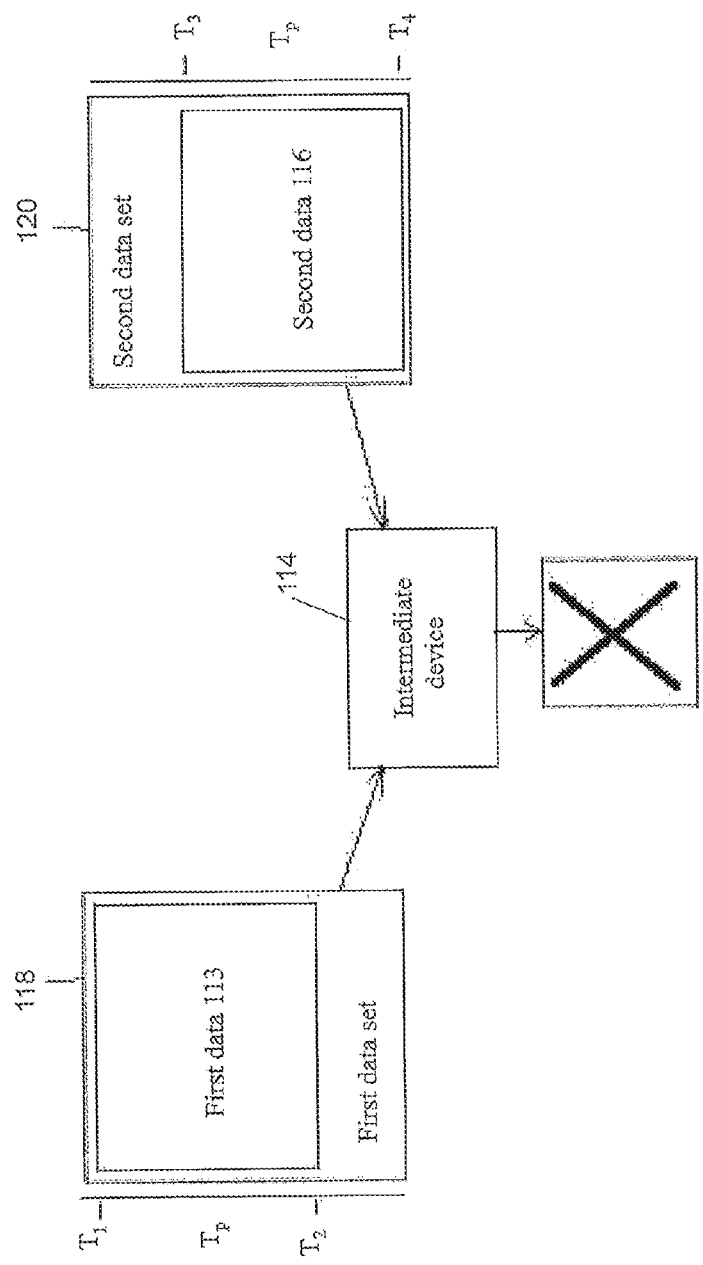
FIG. 5 is a schematic diagram illustrating a method of data synchronization.

In such situations, the data entries of the first data set 118 and the data entries of the second data set 120 may be difficult to integrate because some of the data entries may be associated with the same time when in fact they did not occur at the same time. The report generated from the third data set 122, if assembled from such data sets 118, 120, may be confusing to read and may not accurately portray, for example, the adherence of a patient to a therapy regime. In some configurations, a patient may attempt to integrate data from the first device 102 and the second device 108, where the first device 102 and the second device 108 were used by different patients. In some such configurations, if no two data entries of the third data set 122 are associated with the same time, the report generated from the third data set 122 may still comprise misleading information because data from more than one patient has been utilized in the generation of the report. In some configurations, two successive entries of the third data set 122 may be associated with times that are too far apart from one another to be plausible. For example, the entries may be associated with times that are 50 years apart. In some configurations, and as demonstrated in FIG. 5, the entity performing the method of data integration, for example, the first device 102, the second device 108, and/or the intermediary device 114, may fail to integrate the first data set 118 with the second data set 120 on at least one of the above bases or on some other basis and generate a fault signal and/or error message. The fault signal and/or error message may be added to the report generated from the third data set 122, and/or may be reported to a patient and/or other user through an output module of the entity. In some configurations, if data entries of the first data set 118 are associated with times that match times associated with data entries of the second data set 120, the entity may prompt the user to select a dominant data set that may overwrite parts of the other data set to generate the third data set 122. In some configurations, if data entries of the first data set 118 are associated with times that match times associated with data entries of the second data set 120, the dominant data set may automatically be selected and be used to overwrite the other data set and generate the third data set 122. In some such configurations, the automatic data overwriting procedure may only take place if the temporal length of data overlap (for example, for a given pair of data blocks or for a given pair of data sets) is less than or equal to a predetermined period of time (e.g. 5 minutes). If the temporal length of data overlap is greater than the predetermined period of time, the entity may generate a fault signal or an error message as described above. Individual data entries might be deleted or overwritten in the alternative.

Even if data entries across two or more devices are not coincident in time, they could still be anomalous and require follow up action. For example, two devices that are separated by a significant geographical difference might record data entries with time stamps that are clearly at different times (that is not coincident, even taken into account the time stamp window/tolerance), and record data entries. However, if the time difference is not large/commensurate with the geographical difference, it would be impossible/ implausible for both data entries to be recorded on each device and relate to use by the same patient. For example, if the two medical devices are across town from each other, but have data entries only separated by 5 minutes, clearly there is an error. It would not be possible for the same patient to use one device, record a data entry, drive across town, use the other device and record another time entry all within 5 minutes. It indicates that the clocks are wrong, that different people are using the devices so the data entries do not relate to the same person and/or that data lacks integrity due to incorrect recordal, malfunction in the medical device, and/or inadvertent or deliberate misuse of the medical devices. To compensate for this, a time window can be used (which is similar to but different from the time stamp window). This could be manually or automatically set to a time window/ range that is commensurate to the geographical distance between devices. For example, for devices that are in the same residence, the time range might only be a minute or two. If the devices are in different parts of a city, the time range might be in the order of 20 minutes to an hour or two. If the devices are in different parts of a country or even the world, then the time range could be several hours or days. The time range could be altered as and when the devices move relative to each other. In some configurations, the devices could be tracked using GPS or other tracking technology, and their relative distance determined. The time range could then be set automatically based on the relative distance, for example using a look up table which correlates time ranges for different geographical separations of devices.

In summary, in accordance with certain features, aspects and advantages of at least one of the embodiments disclosed herein, a method for merging or integrating data is disclosed. The method may comprise receiving a first data set from a first device. The first data set may comprise one or more data entries. One or more of the data entries may be related to the use of a first medical device, related to the therapy of a patient using the first medical device, and/or related to a patient using the first medical device. One or more of the data entries may be associated with a time and/or a position in a sequence of entries. In some configurations, each or all of the data entries may be associated with a time and/or position in a sequence of entries. The method may comprise receiving a second data set from a second device. The second data set may comprise one or more data entries. One or more of the data entries may be related to the use of a second medical device, related to the therapy of a patient using the second medical device, and/or related to a patient using the second medical device. One or more of the data entries may be associated with a time and/or a position in a sequence of entries. In some configurations, each or all of the data entries may be associated with a time and/or a position in the sequence of entries. The first data set and the second data set may be integrated. The integration may lead to the creation of a third data set. The integration may be such that the third data set comprises the data entries of the first data set and the second data set. In some configurations, the third data set comprises the data entries of the first data set and the second data set, the data entries ordered or arranged such that they are in a temporal sequence with respect to one another. A report may be generated comprising information related to the third data set and/or information related to a function of the data entries of the third data set.

In some configurations, the first device and/or the second device may be medical devices. In some configurations, both the first and second devices are medical devices. In some configurations, the first device is the first medical device and the second device is the second medical device. In some configurations, the first and/or second devices are PAP devices. In some configurations, the report may comprise information related to the adherence of a patient to a therapy regime. In some configurations, if the third data set comprises more than one data entry associated with the same time, a fault signal may be generated. In some configurations, a data management system may perform the method of data integration. In some such configurations, if the data management system determines that data entries of the first data set are associated with times that are the same as times associated with data entries of the second data set, a fault signal may be generated. In some configurations, if the third data set comprises more than one data entry associated with the same time, the report may comprise an error message. In some configurations, an error or fault may be indicated on the first device, the second device, and/or another device. In some configurations, all of the data entries of the first data set and/or all of the data entries of the second data set may be related to the same information or patient. In some configurations, the third data set may be sent to the first and/or second devices. In some configurations, the third data set may be sent to both the first device and the second device. In some such configurations, the third data set may overwrite the first data set and the second data set. Said in another way, the first and second data sets may be overwritten by the third data set. In some configurations, the function of the data entries of the third data set may comprise an indicator related to the adherence of a patient to a therapy regime. In some such configurations, the indicator may comprise a binary indicator indicating the adherence of the patient to the therapy regime relative to a threshold level of adherence. In some configurations, the indicator may comprise a qualitative indicator indicating the degree of adherence of a patient to a therapy regime. In some configurations, the method of data integration may be performed by the first device and/or by the second device. In some configurations, the method of data integration may be performed by a third device. The third device may be remote from the first device and/or the second device. The third device may comprise a computing system, which may include a network of computers (e.g., computers operating a web application on the internet), a desktop computer, a laptop computer, a tablet, a mobile phone, a 'smart watch' or another device. In some configurations, the first and second data sets may be associated with a patient. In some such configurations, the same patient may be associated with the first and second data sets. In some configurations, if the first and second data sets are not associated with the same patient, the report may comprise an error message. In some configurations, if the first and second data sets are not associated with the same patient, a fault signal may be generated. In some configurations, the report may be uploaded to a removable memory module or a removable media of the first and/or second device.

Additionally, in accordance with certain features, aspects and advantages of at least one of the embodiments disclosed herein, a data management system or apparatus is disclosed. The data management system may comprise a controller. The controller may be configured to receive a first data set from a first device. The first data set may comprise one or more data entries. One or more of the data entries may be related to the use of a first medical device, related to the therapy of a patient using the first medical device, and/or related to a patient using the first medical device. One or more of the data entries may be associated with a time and/or a position in a sequence of entries. In some configurations, each or all of the data entries may be associated with a time and/or a position in a sequence of entries. The controller may be configured to receive a second data set from a second device. The second data set may comprise one or more data entries. One or more of the data entries may be related to the use of a second medical device, related to the therapy of a patient using the second medical device, and/or related to a patient using the second medical device. One or more of the data entries may be associated with a time and/or a position in a sequence of entries. In some configurations, each or all of the data entries may be associated with a time and/or a position in the sequence of entries. The controller may be configured to integrate or merge the first data set and the second data set. The integration may lead to the creation of a third data set. The integration may be such that the third data set comprises the data entries of the first data set and the second data set. In some configurations, the third data set comprises the data entries of the first data set and the second data set. In some configurations, the data entries are ordered or arranged such that they are in a temporal sequence with respect to one another. A report may be generated comprising information related to the third data and/or information related to a function of the data entries of the third data set.

In some configurations, the first device and/or the second device may be medical devices. In some configurations, both the first and second devices are medical devices. In some configurations, the first device is the first medical device and the second device is the second medical device. In some configurations, the first and second devices are PAP devices. In some configurations, the report may comprise information related to the adherence of a patient to a therapy regime. In some configurations, if the data management system determines that data entries of the first data set are associated with times that are the same as times associated with data entries of the second data set, a fault signal may be generated. In some configurations, if the third data set comprises more than one data entry associated with the same time, a fault signal may be generated. In some configurations, if the third data set comprises more than one data entry associated with the same time, the report may comprise an error message. In some configurations, all of the data entries of the first data set and all of the data entries of the second data set may be related to the same information or patient. In some configurations, the third data set may be sent to the first and/or second devices. In some configurations, the third data set may be sent to both the first device and the second device. In some such configurations, the third data set may overwrite the first data set and the second data set. Said in another way, the first and second data sets may be overwritten by the third data set. In some configurations, the function of the data entries of the third data set may comprise an indicator related to the adherence of a patient to the therapy regime. In some such configurations, the indicator may comprise a binary indicator indicating the adherence of the patient to the therapy regime relative to a threshold level of adherence. In some such configurations, the indicator may comprise a qualitative indicator indicating the degree of adherence of a patient to a therapy regime. In some configurations, the method of data integration may be performed by the first device and/or by the second device. In some configurations, the method of data integration may be performed by a third device remote from the first device and the second device. The third device may comprise a computing system, which may include a network of computers (e.g. computers operating a web application on the internet), a desktop computer, a laptop computer, a tablet, a mobile phone, a 'smart watch' and/or another device. In some configurations, the first and second data sets may be associated with a patient. In some such configurations, the same patient may be associated with the first and second data sets. In some configurations, if the first and second data sets are not associated with the same patient, a fault signal may be generated, or if a report is generated, the report may comprise an error message. In some configurations, the report may be uploaded to a removable memory module or a removable media of the first and/or second device.

Figure 10:
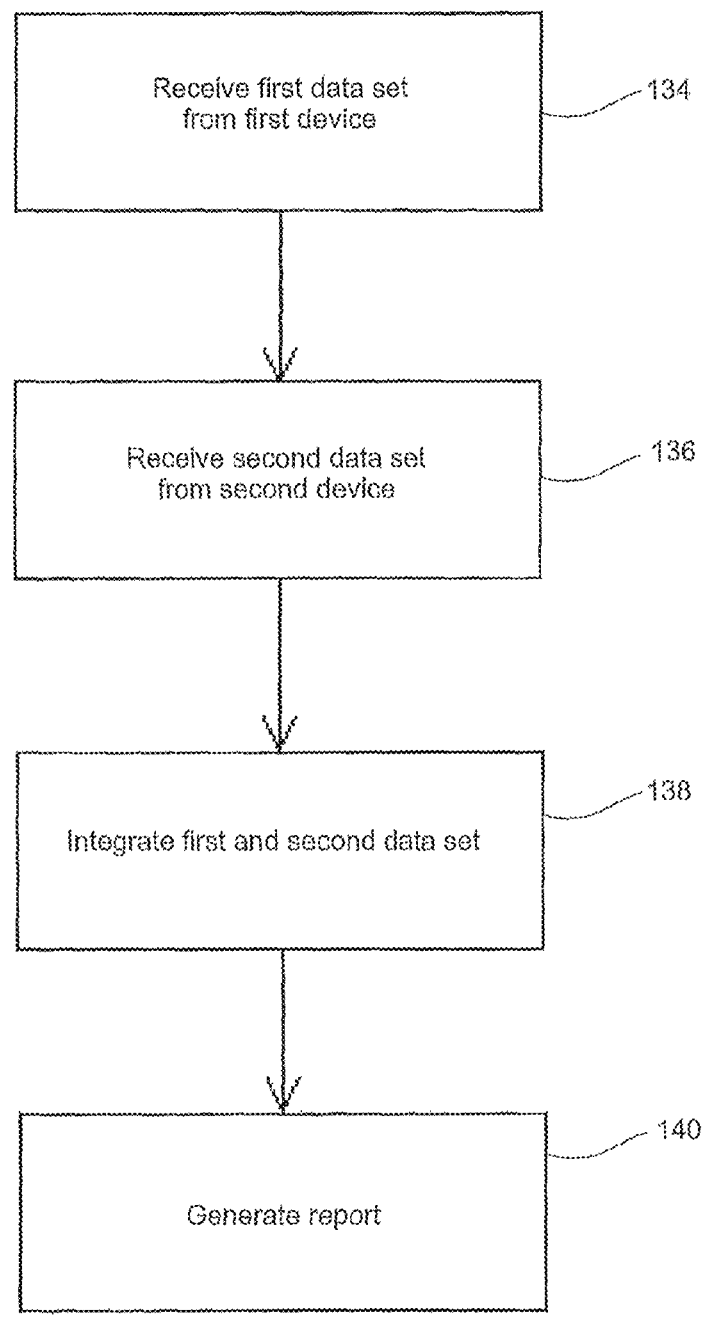
FIG. 10 is a flow chart illustrating certain features, aspects and/or advantages of some configurations of the present disclosure.

To summarize, and with reference to FIG. 10, in some configurations, a method of integrating data is disclosed. In the first step 134, a first data set 118 may be received from a first (medical) device 102, the first data set 118 comprising one or more data entries related to the use of the first device 102, related to a patient using the first device 102, and/or related to the therapy of a patient using the first device 102. Each of the one or more data entries may be associated with a time and/or position in a sequence of entries. In the second step 136, a second data set 120 may be received from a second (medical) device 108, the second data set 120 comprising one or more data entries related to the use of the second device 108, related to a patient using the second device 108, and/or related to the therapy of a patient using the second device 108. In the third step 138, the first data set 118 may be integrated with the second data set 120 to create a third data set 122. The integration may be such that the third data set 122 comprises the data entries of the first and second data sets 118, 120. The data entries may be arranged in a temporal sequence with respect to one another. Optionally, in the fourth step 140, a report may be generated comprising the third data set 122, the data entries of the third data set 122, and/or a function of the data entries of the third data set 122.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of some configurations of the present disclosure have been described with reference to use by a patient or user. However, certain features, aspects and advantages of the data integration method and/or data management system as described may be advantageously practiced by other people on behalf of the patient, including medical professionals, medical device dealers, or medical device providers. Certain features, aspects and advantages of the methods and apparatus of the present disclosure may be equally applied to usage by other people.

Additionally, certain features, aspects, and advantages of some configurations of the present disclosure have been described as usable with PAP devices. However, certain features, aspects and advantages of the data integration method and/or data management system as described may be advantageously practiced with other medical or nonmedical systems or devices such as insulin pumps, glucose monitors, inhalers, and treadmills. Certain features, aspects and advantages of the methods and apparatus of the present disclosure may be equally applied to usage with other devices.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A data management system for use with at least a first breathing assistance apparatus and a second breathing assistance apparatus, the first breathing assistance apparatus and second breathing assistance apparatuses for use by a patient to deliver a CPAP, PAP or flow therapy, the data management system comprising:

a controller which, in operation:

receives, from a first device provided by either the first breathing assistance apparatus associated with a first data communication module or a first proxy device of the first breathing assistance apparatus associated with the first data communication module, a first data set comprising one or more data entries related to the use of the first breathing assistance apparatus by the patient, each of the one or more data entries being associated with a time and/or a position in a sequence of entries;

receives, from a second device provided by either the second breathing assistance apparatus associated with a second data communication module or a second proxy device of the second breathing assistance apparatus associated with the second data communication module, a second data set comprising one or more data entries related to the use of the second breathing assistance apparatus by the patient, each of the one or more data entries being associated with a time and/or a position in a sequence of entries;

integrates the first data set with the second data set to create a third data set, such that the third data set comprises data entries of the first data set and the second data set arranged in a temporal sequence with respect to one another, wherein data entries of the third data set comprises an indicator related to adherence of the patient to a therapy regime and wherein the controller, in operation, further:

generates a fault signal if a data entry of the first data set is associated with a time that is same as a time associated with a data entry of the second data set;

generates a report comprising information related to the third data set, the report comprising an error message if the fault signal has been generated, the report further comprising the indicator related to the adherence of the patient to the therapy regime;

presents to a recipient at least one of the fault signal or the report;

sends the third data set to both the first device and the second device;

overwrites, the first data set and the second data set with the third data set; and wherein at least a data integration function of the controller are provided by at least one of the first device, the second device, or an intermediary device; and wherein the first data communication module and the second data communication module are integrated with the first device and the second device respectively.

2. The data management system of claim 1, wherein the first data communication module and the second data communication module operate to, directly or indirectly, send and receive data pertaining to, respectively, the first device and the second device.

3. The data management system of claim 1, wherein the first device comprises a first peripheral data communication module and/or the second device comprises a second peripheral data communication module, and wherein each of the first peripheral data communication module and/or the second peripheral data communication module is physically or wirelessly connected to its respective device.

4. The data management system of claim 3, wherein when one of the first device or the second device provides at least the data integration function of the controller, data is sent and received between the first data communication module and the second peripheral data communication module of the second device and/or between the second data communication module and the first peripheral data communication module of the first device.

5. The data management system of claim 1, wherein both the first device and the second device comprise a respective peripheral data communication module and wherein the first data communication module and the second data communication module send and receive at least some data relating to their respective device via their respective peripheral data communication module.

6. The data management system of claim 1, wherein when one of the first device or the second device provides at least the data integration function of the controller, the data is sent and received between the first data communication module and the second data communication module.

7. The data management system of claim 6, wherein when one of the first device or the second device provides at least the data integration function of the controller, data is sent and received between a first peripheral data communication module of the first device and a second peripheral data communication module of the second device.

8. The data management system of claim 1, wherein when one of the first device or the second device provides at least the data integration function of the controller, the data is sent and received between the first device and the second device via the intermediary device.

9. The data management system of claim 1, wherein the intermediary device is one of
   a. a further breathing assistance apparatus;
   b. a remote computing system; and
   c. a wide area network.

10. The data management system of claim 1, wherein the intermediary device is a desktop computer, a laptop computer, a tablet, a mobile phone, or a wearable computing system.

11. The data management system of claim 1, wherein when one of the first device or the second device provides at least the data integration function of the controller, the data management system comprises a peripheral data storage medium, insertable into an accessory compartment of that one of the first device and the second device which does not provide the data integration function of the controller, to store the data set of that device on the peripheral data storage medium, wherein the peripheral data storage medium is then insertable into an accessory compartment of that other one of the first device and the second device which provides the data integration function of the controller, to enable that other device to integrate the respective data sets into the third data set, wherein the third data set is stored on the peripheral data storage medium such that the peripheral data storage medium having the third data set is providable to the recipient.

12. The data management system of claim 1, wherein the report further comprises the third data set and/or a function of the data entries of the third data set.

13. The data management system of claim 1, wherein the indicator comprises:
   a binary indicator indicating the adherence of the patient to the therapy regime relative to a threshold level of adherence; or
   a qualitative indicator related to a degree of adherence of the patient to the therapy regime.

14. The data management system of claim 1, wherein the first device and the second device, in operation, further communicates wirelessly with each other or via NFC.

15. The data management system of claim 1, wherein the first device is a home treatment device to treat a condition at home and/or wherein the second device is a travel-friendly device.

16. The data management system of claim 1, wherein the first device comprises a clock and the second device comprises a clock, wherein the controller of the data management system in operation further synchronizes the clock in the first device with the clock in the second device, and wherein the clock in the first device and the clock in the second device are synchronized by coupling the first device and the second device or by using external time signals such as GPS timing signals.

17. The data management system of claim 1, wherein the controller in operation further determines plausibility of data entries from the first device and the second device based on a time difference between time stamps of data entries from respective data sets from the first device and the second device, and respective geographical locations of the first device and the second device.

18. The data management system of claim 1, wherein when one of the first device or the second device provides at least the data integration function of the controller, that one of the first device and the second device performing the data integration function of the controller comprises an output interface.

19. The data management system of claim 18, wherein the output interface is configured to:
- present to the recipient at least one of the fault signal or the report, and/or
- display a query for confirmation prior to integrating the first data set and the second data set; wherein an input interface is configured to receive a response to the query, the response comprising a positive or negative response to the query in order to authorize or decline the integration of the first data set and the second data set.

20. The data management system of claim 19, wherein the query is displayed upon detection of insertion of a peripheral data storage medium into the controller.

* * * * *